(12) United States Patent
Livorsi et al.

(10) Patent No.: US 10,285,826 B2
(45) Date of Patent: May 14, 2019

(54) SURGICAL INSTRUMENT AND METHOD OF POSITIONING AN ACETABULAR PROSTHETIC COMPONENT

(71) Applicant: DEPUY SYNTHES PRODUCTS, INC., Raynham, MA (US)

(72) Inventors: Carl F. Livorsi, Lakeville, MA (US); Francisco A. Amaral, Acushnet, MA (US); Rod G. Cameron, Franklin, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 200 days.

(21) Appl. No.: 15/175,075

(22) Filed: Jun. 7, 2016

(65) Prior Publication Data

US 2016/0278941 A1    Sep. 29, 2016

Related U.S. Application Data

(62) Division of application No. 13/434,154, filed on Mar. 29, 2012, now Pat. No. 9,358,130.

(51) Int. Cl.
*A61F 2/46* (2006.01)
*A61B 90/00* (2016.01)
*A61F 2/30* (2006.01)

(52) U.S. Cl.
CPC .......... *A61F 2/4657* (2013.01); *A61B 90/06* (2016.02); *A61F 2/4609* (2013.01);
(Continued)

(58) Field of Classification Search
CPC .... A61F 2/4657; A61F 2/4609; A61F 2/4603; A61F 2/46; A61F 2002/4668;
(Continued)

(56) References Cited

U.S. PATENT DOCUMENTS

| 534,434 A | 2/1895 | Frost |
|---|---|---|
| 1,942,640 A | 1/1934 | Fromme |

(Continued)

FOREIGN PATENT DOCUMENTS

| DE | 10202582 C1 | 9/2003 |
|---|---|---|
| EP | 1920713 A2 | 5/2008 |

(Continued)

OTHER PUBLICATIONS

Japanese Office Action with English translation, Japanese Application No. 2013-068417 dated Jan. 10, 2017, 11 pages.

(Continued)

*Primary Examiner* — Matthew J Lawson
*Assistant Examiner* — Amy R Sipp
(74) *Attorney, Agent, or Firm* — Barnes & Thornburg LLP (57) ABSTRACT

An orthopedic surgical instrument for positioning an acetabular prosthetic component in a patient's surgically-prepared acetabulum includes a surgical tool configured to be coupled to the acetabular prosthetic component, and a gravity-based position indicator removably coupled to the surgical tool. The position indicator includes a first marking indicating a first position of the acetabular prosthetic component, and a second marking indicating a second position.

16 Claims, 9 Drawing Sheets

(52) U.S. Cl.
CPC .............. *A61B 2090/068* (2016.02); *A61F 2002/30617* (2013.01); *A61F 2002/4627* (2013.01); *A61F 2002/4629* (2013.01); *A61F 2002/4668* (2013.01)

(58) Field of Classification Search
CPC .............. A61B 90/06; A61B 2090/067; A61B 2090/068; A61B 2090/069
See application file for complete search history.

(56) References Cited

U.S. PATENT DOCUMENTS

| | | | |
|---|---|---|---|
| 2,379,796 | A | 7/1945 | Freeman et al. |
| 4,716,894 | A | 1/1988 | Lazzeri et al. |
| 5,061,270 | A | 10/1991 | Aboczky et al. |
| D331,461 | S | 12/1992 | Lester |
| 5,250,051 | A | 10/1993 | Maryan |
| 5,284,483 | A | 2/1994 | Johnson |
| 5,320,625 | A * | 6/1994 | Bertin ............... A61B 5/22 606/91 |
| 5,364,403 | A | 11/1994 | Petersen et al. |
| 5,457,857 | A | 10/1995 | Lam |
| 5,540,697 | A | 7/1996 | Rehmann et al. |
| 5,584,837 | A | 12/1996 | Petersen |
| 5,658,294 | A * | 8/1997 | Sederholm ............... A61F 2/34 606/91 |
| 5,683,399 | A | 11/1997 | Jones et al. |
| 5,836,081 | A * | 11/1998 | Orosz, Jr. ............... A61B 5/0215 33/290 |
| 6,102,915 | A * | 8/2000 | Bresler ............... A61F 2/4609 606/80 |
| 6,395,005 | B1 | 5/2002 | Lovell |
| 6,743,235 | B2 | 6/2004 | Subba Rao |
| 7,037,310 | B2 | 5/2006 | Murphy |
| 8,454,619 | B1 * | 6/2013 | Head ............... A61B 17/1746 606/91 |
| 8,469,962 | B1 * | 6/2013 | Head ............... A61B 17/1746 606/91 |
| 8,764,758 | B2 | 7/2014 | Echeverri |
| 9,095,448 | B2 | 8/2015 | Birkbeck et al. |
| 2002/0125756 | A1 | 9/2002 | Asano |
| 2003/0181919 | A1 * | 9/2003 | Gorek ............... A61B 17/1757 606/96 |
| 2003/0199882 | A1 * | 10/2003 | Gorek ............... A61B 17/1757 606/104 |
| 2004/0073225 | A1 * | 4/2004 | Subba Rao ............... A61F 2/4609 606/91 |
| 2004/0092944 | A1 * | 5/2004 | Penenberg ............... A61F 2/3609 606/91 |
| 2004/0152972 | A1 | 8/2004 | Hunter |
| 2004/0243148 | A1 * | 12/2004 | Wasielewski ............... A61B 17/00 606/130 |
| 2005/0033315 | A1 * | 2/2005 | Hankins ............... A61B 90/11 606/129 |
| 2005/0107799 | A1 | 5/2005 | Graf et al. |
| 2005/0149054 | A1 * | 7/2005 | Gorek ............... A61B 17/1757 606/104 |
| 2006/0095047 | A1 * | 5/2006 | de la Barrera ............... A61F 2/4657 606/102 |
| 2006/0184177 | A1 | 8/2006 | Echeverri |
| 2007/0149878 | A1 * | 6/2007 | Hankins ............... A61B 8/0841 600/427 |
| 2010/0087823 | A1 * | 4/2010 | Kondrashov ............... A61B 17/025 606/79 |
| 2010/0137871 | A1 | 6/2010 | Borja |
| 2010/0249657 | A1 | 9/2010 | Nycz et al. |
| 2011/0027100 | A1 | 2/2011 | Cummane et al. |
| 2011/0060339 | A1 * | 3/2011 | de Wekker ............... A61B 5/1071 606/80 |
| 2011/0184419 | A1 | 7/2011 | Meridew et al. |
| 2011/0276053 | A1 * | 11/2011 | Birkbeck ............... A61F 2/4609 606/91 |
| 2012/0330319 | A1 * | 12/2012 | Birkbeck ............... A61F 2/4609 606/91 |
| 2013/0046310 | A1 * | 2/2013 | Ranawat ............... A61F 2/4609 606/91 |
| 2013/0053859 | A1 * | 2/2013 | Penenberg ............... A61B 17/164 606/91 |
| 2013/0053904 | A1 * | 2/2013 | Penenberg ............... A61B 17/1659 606/86 R |
| 2014/0378984 | A1 | 12/2014 | Birkbeck et al. |

FOREIGN PATENT DOCUMENTS

| | | |
|---|---|---|
| WO | 2001030247 A1 | 5/2001 |
| WO | 2003057087 A2 | 7/2003 |
| WO | 2004030556 A2 | 4/2004 |
| WO | 2005046475 A1 | 5/2005 |
| WO | 2010128320 A1 | 11/2010 |
| WO | 2010145769 A1 | 12/2010 |
| WO | 2011095804 A1 | 8/2011 |

OTHER PUBLICATIONS

Depuy International Ltd., Pinnacle Acetabular Cup System Surgical Technique; Cat. No. 9068-80-050, 2003, 40 pages.
Depuy International Ltd., Pinnacle Acetabular Cur System Surgical Technique; Cat. No. 9068-80-050 version 2; Jun. 2009, 36 pages.
DePuy International Ltd. Pinnacle Acetabular Cup System Surgical Technique; Cat. No. 0611-42-050 (Rev. 3); Aug. 24, 2004, 49 pages.
Langston, et al., "The Effect of Component Size and Orientation on the Concentrations of Metal Ions After Resurfacing Arthroplasty of the Hip," The Journal of Bone & Joint Surgery, pp. 1143-1152, vol. 90-B, No. 9, Sep. 2008.
Murray, D.W., "The Definition and Measurement of Acetabular Orientation," The Journal of Bone & Joint Surgery, pp. 228-232, vol. 75-B, No. 2, Mar. 1993.
European Search Report for European Application No. 13161262. 4-1654, dated Jun. 20, 2013, 8 pages.
L. Fabeck, et al., "A Method to Measure Acetabular Cup Anteversion After Total Hip Replacement,", Acta Orthopaedica Belgica. vol. 65—4—1999, 485-491.
Pinnacle Acetabular Cup System, Surgical Technique; 2002, 49 pages, DePuy Orthopaedics, Inc.

* cited by examiner

Fig. 12 ial application claims priority to U.S. patent application Ser. No. 13/434,154, which was filed on Mar. 29, 2012 and is expressly incorporated herein by reference.

SURGICAL INSTRUMENT AND METHOD OF POSITIONING AN ACETABULAR PROSTHETIC COMPONENT

This divisional application claims priority to U.S. patent application Ser. No. 13/434,154, which was filed on Mar. 29, 2012 and is expressly incorporated herein by reference.

TECHNICAL FIELD

The present disclosure relates generally to orthopaedic surgical instruments and, more particularly, to surgical instruments used to trial and install an acetabular prosthetic component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments.

SUMMARY

According to one aspect of the disclosure, an orthopaedic surgical instrument for positioning an acetabular prosthetic component in a patient's surgically-prepared acetabulum is disclosed. The orthopaedic surgical instrument includes a shaft having a first end configured to be coupled to the acetabular prosthetic component, a handle attached to the shaft at a second end opposite the first end, and a bubble indicator attached to the shaft between the first end and the second end. The bubble indicator has a face and a plurality of markings defined on the face. The plurality of markings include a first marking indicating a first abduction angle, and a second marking indicating a second abduction angle and an anteversion angle of the acetabular prosthetic component.

In some embodiments, the second abduction angle may be less than the first abduction angle. In some embodiments, the first abduction angle may be approximately 45 degrees. Additionally, in some embodiments, the second abduction angle may be approximately 40 degrees. In some embodiments, the anteversion angle may be equal to approximately 15 degrees of rotation about a transverse axis extending through the patient.

In some embodiments, the bubble indicator may be detachable from the shaft. In some embodiments, the first marking and the second marking may be customized patient-specific markings.

In some embodiments, the face may be circular and have a center point. The first marking may be located approximately at the center point of the face. Additionally, in some embodiments, the second marking may be offset from the center point of the face.

In some embodiments, the first marking may include a graphical indicator and a numerical indicator of the first abduction angle.

According to another aspect, the orthopaedic surgical instrument includes a surgical tool configured to be coupled to the acetabular prosthetic component, and a gravity-based position indicator removably coupled to the surgical tool. The position indicator includes a first marking indicating a first position of the acetabular prosthetic component in the patient's surgically-prepared acetabulum, and a second marking indicating a second position of the acetabular prosthetic component in the patient's surgically-prepared acetabulum.

In some embodiments, the first marking may indicate a first abduction angle, and the second marking may indicate a second abduction angle. The second abduction angle may be different from the first abduction angle. In some embodiments, the surgical tool may have an aperture defined therein, and the position indicator may include a rod shaped to match the aperture of the surgical tool such that the position indicator is coupled to the surgical tool in a single predetermined orientation.

In some embodiments, the surgical tool may have a plurality of external threads formed on one end. The plurality of external threads may correspond to a plurality of internal threads of the acetabular prosthetic component to permit the surgical tool to be threadingly engaged with the acetabular prosthetic component.

According to another aspect, a method of positioning an acetabular prosthetic component in a patient's surgically-prepared acetabulum is disclosed. The method includes rotating the acetabular prosthetic component in the patient's surgically-prepared acetabulum until a bubble of a bubble indicator is substantially aligned with a first marking. The first marking indicates a first position of the acetabular prosthetic component. The method also includes rotating the acetabular prosthetic component anteriorly until the bubble is substantially aligned with a second marking. The second marking indicates a second position of the acetabular prosthetic component.

In some embodiments, the acetabular prosthetic component may be at a first abduction angle in the first position, and the acetabular prosthetic component may be at a second abduction angle in the second position. The second abduction angle may be less than the first abduction angle.

In some embodiments, the first abduction angle may be approximately 45 degrees. Additionally, in some embodiments, the second abduction angle may be approximately 40 degrees. In some embodiments, rotating the acetabular prosthetic component anteriorly may include rotating the acetabular prosthetic cup approximately 15 degrees about a transverse axis extending through the patient.

In some embodiments, the method may further include rotating the acetabular prosthetic component in the patient's surgically-prepared acetabulum until the bubble is substantially aligned with a third marking. The third marking may correspond to a third position of the acetabular prosthetic cup.

In some embodiments, the method may further include selecting the bubble indicator from a plurality of bubble indicators, attaching the bubble indicator to a surgical tool, and threading the acetabular prosthetic component onto the surgical tool.

Additionally, in some embodiments, rotating the acetabular prosthetic component in the patient's surgically-prepared acetabulum until the bubble of the bubble indicator is substantially aligned with a first marking may include aligning a graphical indicator of the first marking with the bubble of the bubble indicator.

In some embodiments, the method may also include positioning the bubble indicator in a coronal plane defined by the patient's body such that the first marking is aligned with the coronal plane. Rotating the acetabular prosthetic component in the patient's surgically-prepared acetabulum may include maintaining alignment between the first marking and the coronal plane.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
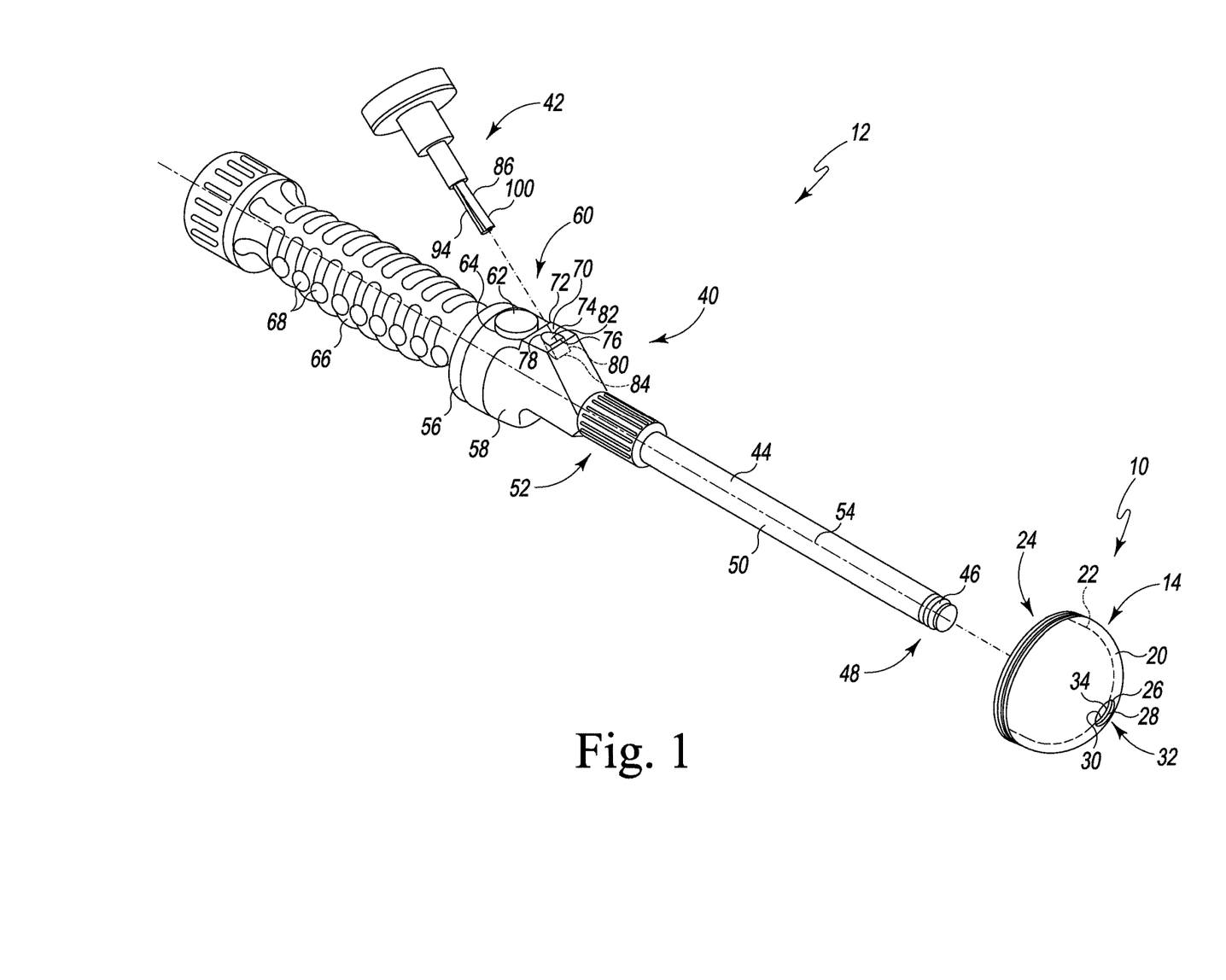
FIG. 1 is an exploded perspective view of an orthopaedic surgical instrument assembly and an acetabular prosthetic component.

Referring to FIG. 1, an acetabular prosthetic component 10 and an orthopaedic surgical instrument assembly 12 (hereinafter assembly 12) are shown. The assembly 12 may be used during a hip arthroplasty surgical procedure to trial and install the acetabular prosthetic component 10 in a patient's bone. It should be appreciated, however, that although the assembly 12 is described below in regard to the performance of a hip arthroplasty surgical procedure, certain concepts associated with the assembly 12 may be utilized in replacement procedures of numerous other joints throughout the body. In other words, one or more of the elements of the assembly 12 may be incorporated into surgical instruments used in, for example, knee, spinal, shoulder, or other replacement procedures.

The acetabular prosthetic component 10 includes an acetabular shell component 14 configured to be implanted within a surgically-prepared acetabulum 16 (see FIG. 5) of a patient. The acetabular shell component 14 includes an outer surface 20 having a convex shape that is hemispherical or partially spherical. The acetabular shell component 14 also includes an inner surface 22 having a concave shape that is partially spherical in shape. The inner surface 22 defines a cavity 24 in the acetabular shell component 14 that is sized to receive a metallic or polymeric insert.

The acetabular shell component 14 has an opening 26 defined in the outer surface 20, and an inner wall 28 extends inwardly from the opening 26 to an opening 30 defined in the inner surface 22. The inner wall 28 defines a passageway 32 through the acetabular shell component 14. As shown in FIG. 1, the inner wall 28 has a plurality of internal threads 34 defined thereon.

The orthopaedic surgical instrument assembly 12 includes a surgical tool 40 and a position indicator 42. In the illustrative embodiment, the surgical tool 40 is an impaction tool. It should be appreciated that in other embodiments the surgical tool 40 may be a positioning tool or other surgical device configured to be secured to the acetabular prosthetic component 10. The surgical tool 40 has a shaft 44 that includes a plurality of external threads 46 corresponding to the threads 34 of the acetabular shell component 14. As shown in FIG. 1, the external threads 46 are defined at an end 48 of the shaft 44 such that the acetabular shell component 14 may be threaded onto the end 48 of the shaft 44, thereby coupling the acetabular shell component 14 to the surgical tool 40 for trialing or implantation.

The shaft 44 of the surgical tool 40 has a cylindrical body 50 that extends from the end 48 to an end 52 and defines a longitudinal axis 54. The surgical tool 40 includes a handle 56 that is coupled to the end 52 of the shaft 44. As shown in FIG. 1, the handle 56 includes a handle body 58, and, in the illustrative embodiment, the shaft 44 is operable to pivot about the longitudinal axis 54 relative to the handle body 58.

The surgical tool 40 also includes a locking mechanism 60 configured to prevent the shaft 44 from pivoting about the axis 54. The locking mechanism 60 is positioned in the handle body 58 and includes a button 62 positioned in an opening 64 defined in the handle body 58. A user may operate the button 62 to release the locking mechanism 60 such that the shaft 44 may be pivoted about the axis 54. It should be appreciated that in other embodiments the locking mechanism 60 may include a switch, tab, or other user-operated device to release and lock the shaft 44 relative to the handle body 58. It should be appreciated that in other embodiments the shaft 44 and the handle 56 may be formed as a single monolithic component such that the shaft 44 does not pivot or rotate relative to the handle 56.

As shown in FIG. 1, the handle 56 of the surgical tool 40 also includes a grip 66 secured to the handle body 58. The grip 66 includes a knurled outer surface 68 that is sized to receive the hand of a surgeon or other user. It should be appreciated that in other embodiments the outer surface may be substantially smooth or include a number of ribs to support the hand of a user.

The handle body 58 of the surgical tool 40 also includes a platform 70 configured to receive the position indicator 42. The platform 70 has an upper surface 72, and an opening 74 is defined in the upper surface 72. As shown in FIG. 1, the opening 74 is defined by a substantially straight edge 76 and a curved or rounded edge 78. A substantially planar inner wall 80 slopes inwardly from the edge 76. The inner wall 80 cooperates with a curved inner wall 82 that slopes inwardly from the rounded edge 78 to define an aperture 84 in the handle body 58. As described in greater detail below, the aperture 84 is sized and shaped to receive a rod 86 of the position indicator 42.

Figure 2:
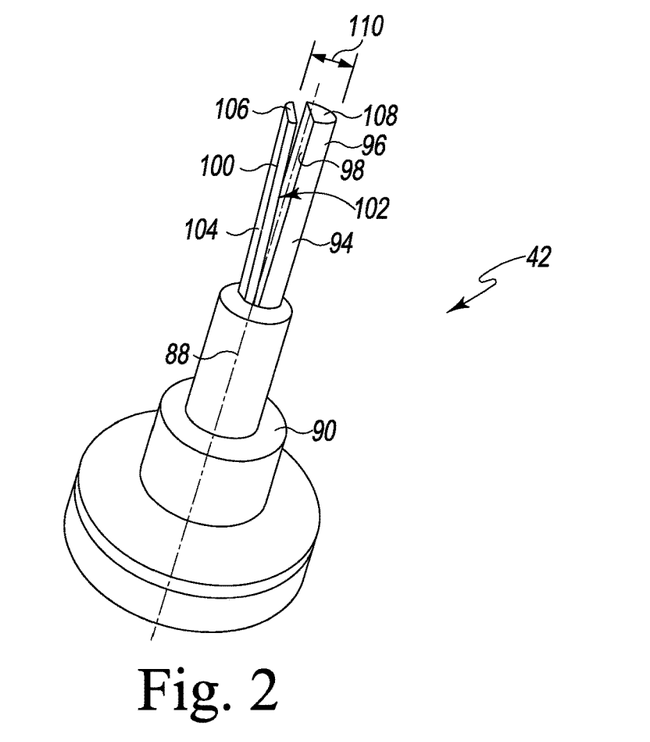
FIG. 2 is a perspective view of one embodiment of a position indicator of the orthopaedic surgical instrument assembly of FIG. 1.

Referring now to FIG. 2, the position indicator 42 of the assembly 12 has a longitudinal axis 88 that extends a housing 90 and the rod 86, which is secured to a lower end 92 of the housing 90. The rod 86 includes a cantilevered support arm 94 that extends from the lower end 92 of the housing 90. The support arm 94 has a curved outer surface 96 that is shaped to match the curved inner wall 82 of the handle body 58. The support arm 94 has a substantially planar surface 98 that is positioned opposite the outer surface 96.

The rod 86 of the position indicator 42 also includes a cantilevered spring arm 100 that extends from the lower end 92 of the housing 90. The spring arm 100 includes a substantially planar surface 102 that faces the surface 98 of the support arm 94. The spring arm 100 also includes another substantially planar surface 104, which is positioned opposite the surface 102. The surface 104 of the spring arm 100 is shaped to match the substantially planar inner wall 80 of the handle body 58.

In the illustrative embodiment, the spring arm 100 of the rod 86 is configured to flex and move relative to the support arm 94 between an uncompressed position and a compressed position. As shown in FIG. 2, the tip 106 of the spring arm 100 and the tip 108 of the support arm 94 define an uncompressed thickness 110 of the rod 86. The uncompressed thickness 110 is greater than the size of the opening 74 of the handle body 58.

Figure 4:
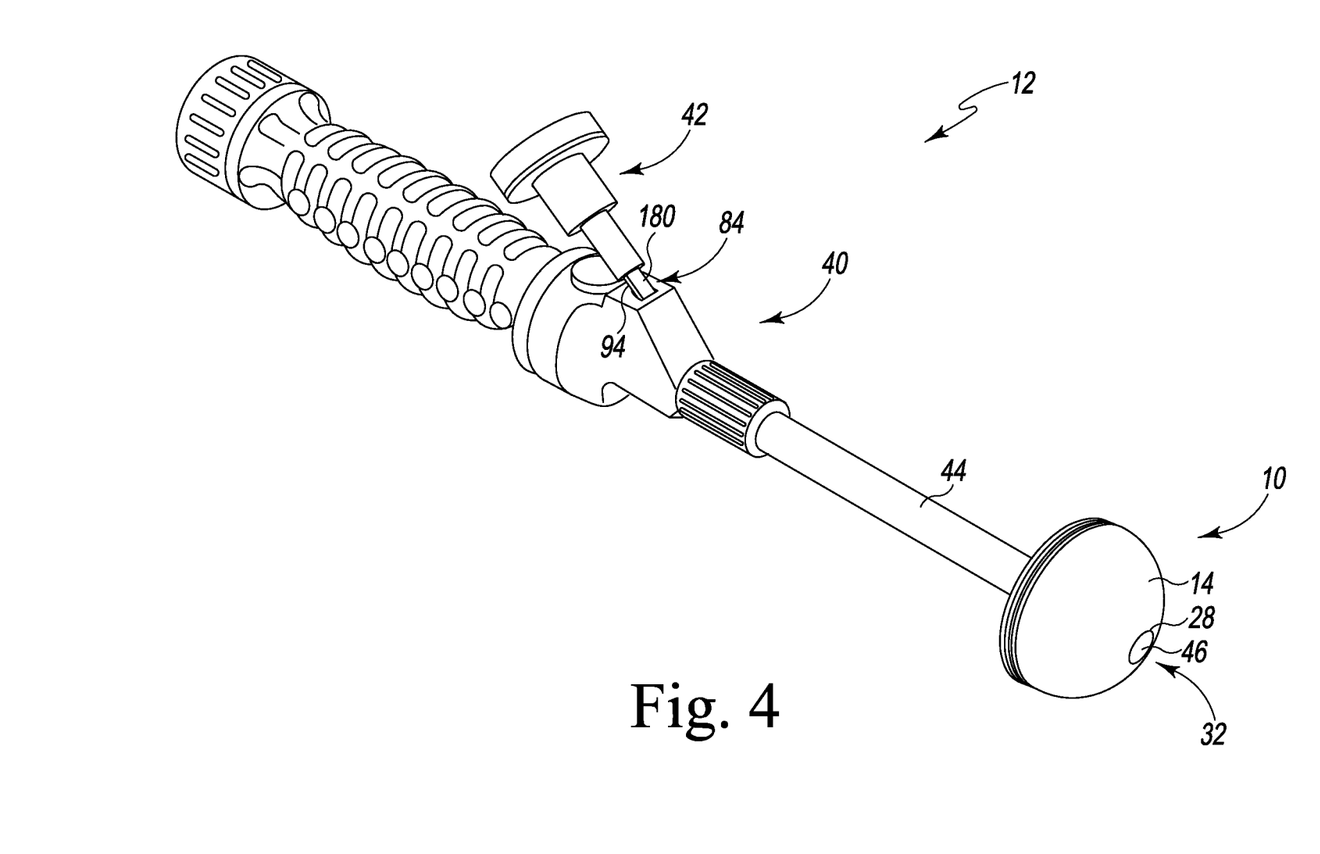
FIG. 4 is a perspective view of the orthopaedic surgical instrument assembly of FIG. 1.

To attach the position indicator 42 to the surgical tool 40, the rod 86 is advanced into the aperture 84 defined in the handle body 58. The arms 94, 100 of the rod 86 are advanced into contact with the inner walls 82, 80, respectively, of the handle body 58 that define the aperture 84. When the spring arm 100 engages the inner wall 80, the spring arm 100 moves relative to the support arm 94 from the uncompressed position to the compressed position, thereby permitting the rod 86 to advance along the inner walls 82, 80 of the handle body 58. When the position indicator 42 is attached to the surgical tool 40 as shown in FIG. 4, the spring arm 100 acts as a biasing element to prevent inadvertent detachment of the position indicator 42 from the handle body 58.

The arms 94, 100 of the rod 86 are keyed to match the shape of the aperture 84 such that the position indicator 42 is located in a single predetermined orientation relative to the surgical tool 40. It should be appreciated that in other embodiments the rod of the position indicator 42 may be a single shaft that is similarly keyed to match the structure of the aperture of the handle body 58. Additionally, in other embodiments, the aperture may be cylindrical and the rod may have a single cylindrical shaft sized to be received in the aperture. In other embodiments, the position indicator and the surgical tool may be configured such that the position indicator is permitted to rotate about its axis 88 between multiple predetermined positions.

It should also be appreciated that in other embodiments the assembly 12 may include other locking mechanisms, such as, for example, latches, pins, threaded fasteners, and other retention devices to secure the position indicator to the handle body. It should also be appreciated that in other embodiments the position indicator 42 may be fixed to the handle body 58 such that the position indicator 42 cannot be detached from the handle body 58 during normal use.

Figure 3:
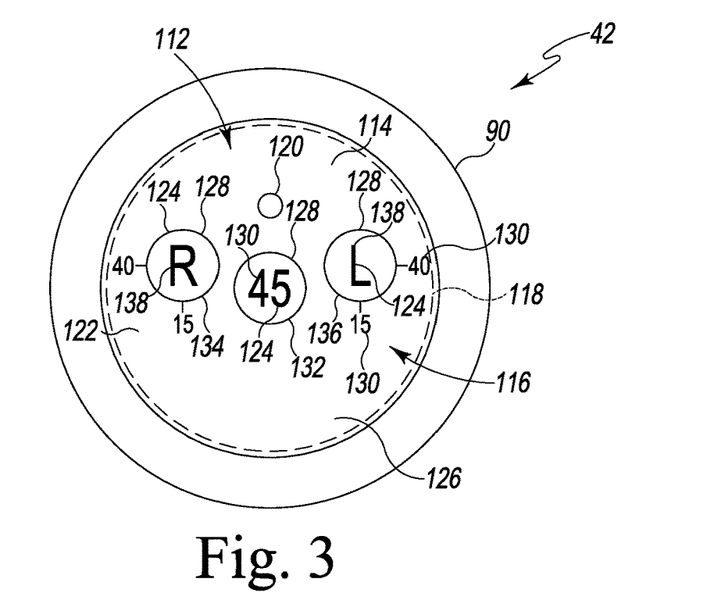
FIG. 3 is a front elevation view of the position indicator of FIG. 2.

Referring now to FIG. 3, the position indicator 42 of the assembly 12 includes a housing 90 having a gravity-based indicator 112 secured thereto. As used herein, a "gravity-based indicator" is a sensor that indicates position based on gravity. In the illustrative embodiment, the gravity-based indicator 112 is a bubble indicator 114. In other embodiments, the gravity-based indicator 112 may be a tilt sensor, including, for example, an enclosed shallow dish filled with fluid. A ball bearing is positioned in the shallow dish and is configured to move based on the angle or tilt of the shallow dish.

The bubble indicator 114 of the position indicator 42 includes a vial 116 that defines a chamber 118 filled with a fluid such as, for example, isopropyl alcohol. In the illustrative embodiment, the vial 116 defines a dome-shaped chamber 118. A bubble 120 is trapped within the chamber 118. Gravity and the physical difference between the gas of the bubble 120 and the fluid in the chamber 118 control the function of the bubble indicator 114, with the bubble 120 floating toward the side of the vial 116 that constitutes the high side of the vial 116.

The vial 116 of the bubble indicator 114 has a face plate 122 that is substantially transparent. In that way, a user may look through the face plate 122 to determine the position of the bubble 120. As shown in FIG. 3, the bubble indicator 114 has a plurality of markings 124 etched into an outer surface 126 of the face plate 122. Each of the markings 124 indicates a predetermined position of the acetabular prosthetic component 10 within the patient's surgically-prepared acetabulum 16.

In the illustrative embodiment, the markings 124 of the bubble indicator 114 include a plurality of graphical indicators 128 that correspond to the plurality of predetermined positions of the acetabular prosthetic component 10. The markings 124 also include a plurality of numerical indicators 130 that are associated with the graphical indicators 128. As shown in FIG. 3, the graphical indicators 128 include rings 132, 134, 136, and the bubble 120 is configured to align with each of the rings 132, 134, 136 based on the position of the acetabular prosthetic component 10 within the patient's surgically-prepared acetabulum 16, as described in greater detail below. The markings 124 further include side indicators 138, which associate the graphical indicators 128 and the numerical indicators 130 with a particular side of a patient's body (i.e., right or left).

The housing 90 of the position indicator 42 is formed from an implant grade metallic material, such as, for example, aluminum or titanium. The vial 116 is sealed within the housing 90 such that the position indicator 42 may be autoclaved for multiple uses. In other embodiments the housing 90 may be molded from a polymeric material, such as, for example, plastic. It should be appreciated that the position indicator 42 may be a reusable or disposable surgical instrument.

Figure 5:
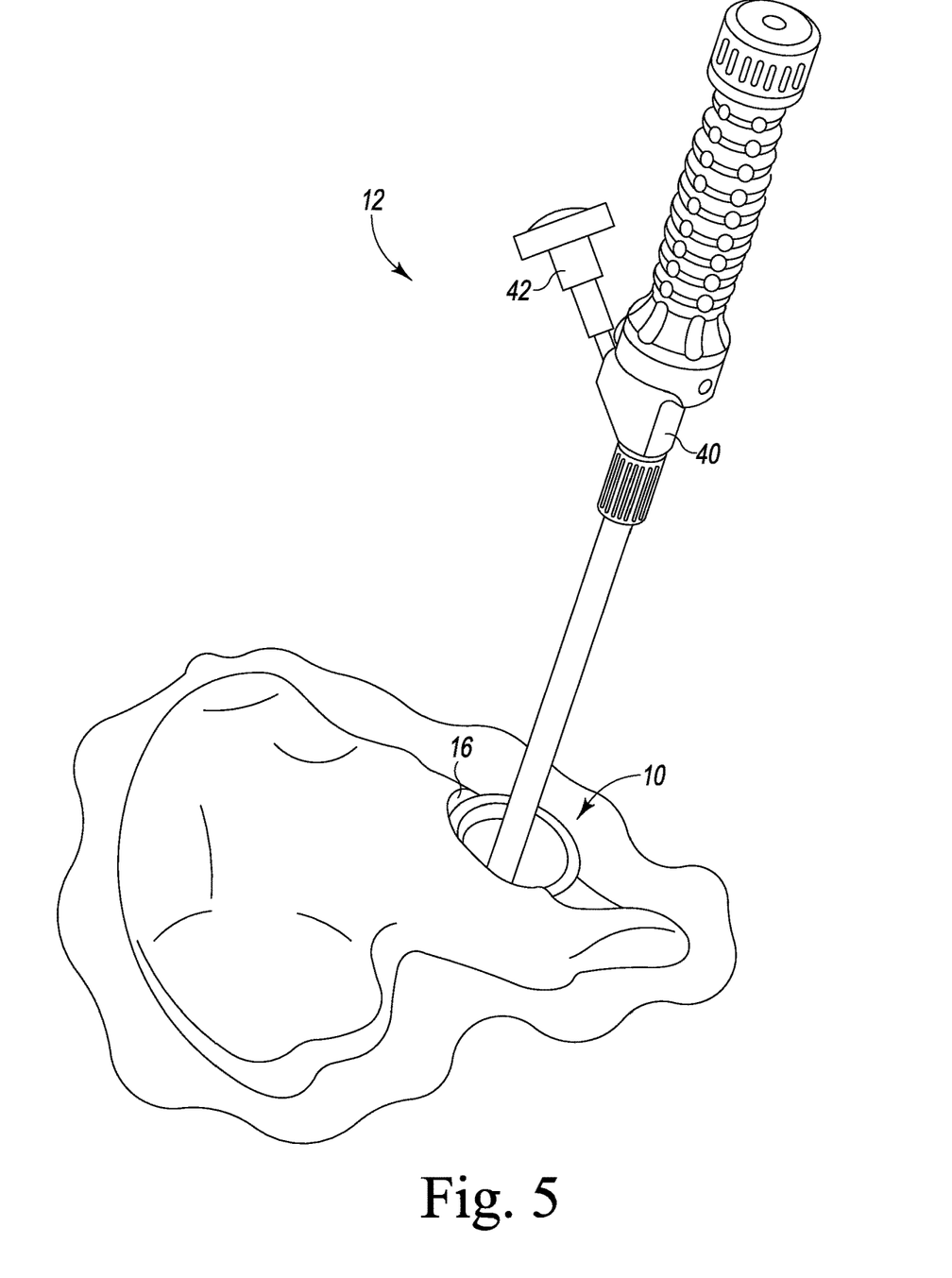
FIG. 5 is a perspective view of the orthopaedic surgical instrument assembly secured to the acetabular prosthetic component, which is positioned in a patient's surgically-prepared acetabulum.
Figure 6:
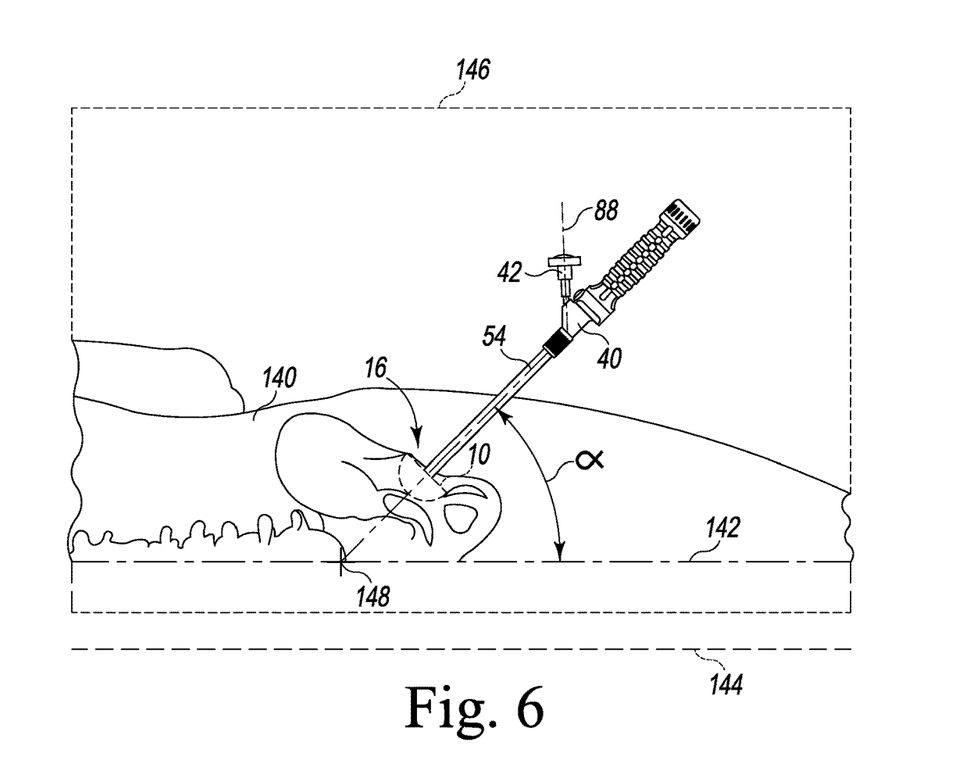
FIG. 6 is an elevation view of the orthopaedic surgical instrument assembly and the acetabular prosthetic component in a predetermined position.
Figure 8:
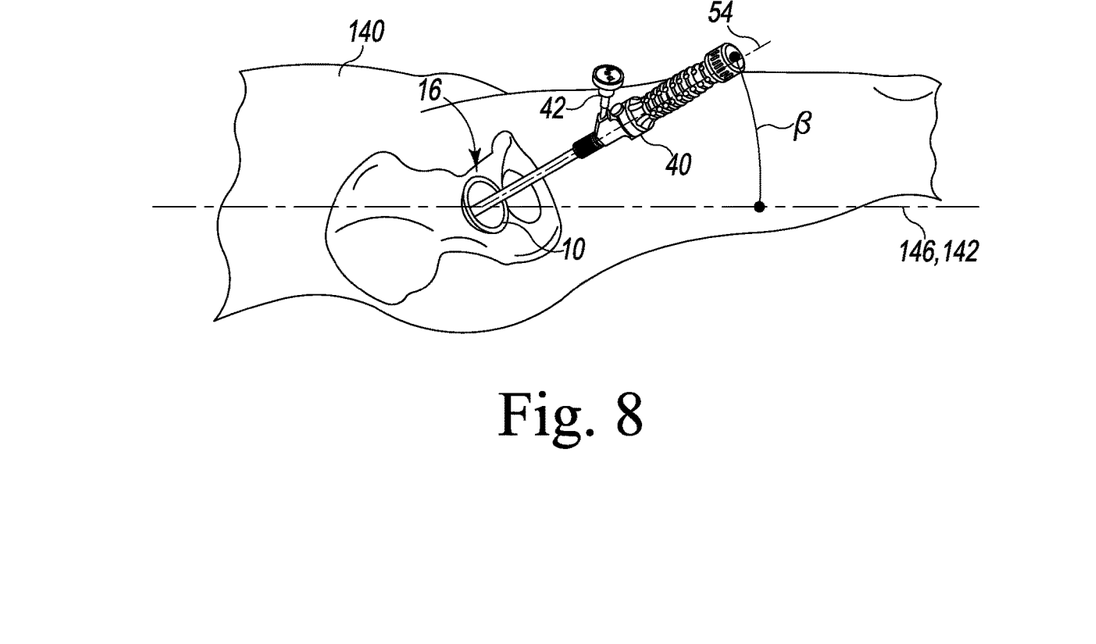
FIG. 8 is a plan view of the orthopaedic surgical instrument assembly and the acetabular prosthetic component in another predetermined position.
Figure 10:
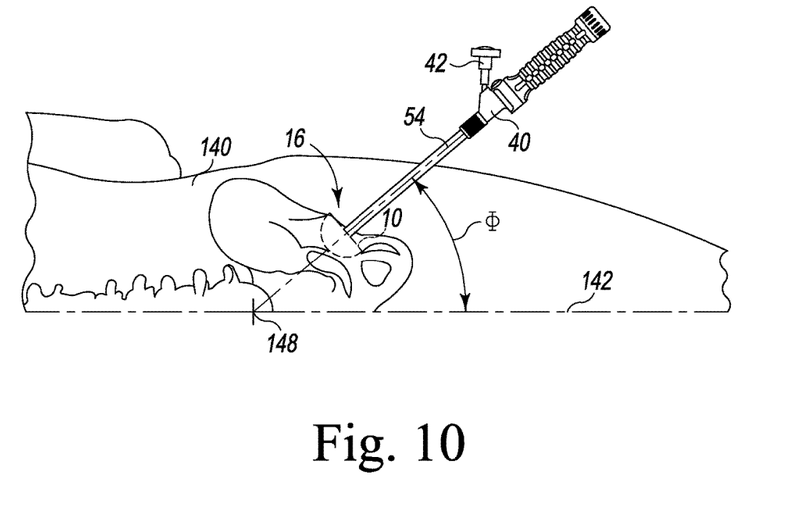
FIG. 10 is an elevation view of the orthopaedic surgical instrument assembly and the acetabular prosthetic component in the predetermined position of FIG. 8.

In use, a surgeon or other user may utilize the assembly 12 to trial and implant the acetabular prosthetic component 10. To do so, the surgical tool 40 is assembled with the position indicator 42 and the acetabular prosthetic component 10, as shown in FIG. 4. As shown in FIGS. 5 and 6, the surgical tool 40 may be used to position the acetabular prosthetic component 10 within the patient's acetabulum 16 at an initial predetermined position at a predetermined abduction angle. As shown in FIGS. 8 and 10, the surgical tool 40 may be used to position the acetabular prosthetic component 10 within the patient's acetabulum 16 at another predetermined position at another predetermined abduction angle.

As shown in FIG. 4, the position indicator 42 may be attached to the tool 40. As described above, the rod 86 of the position indicator 42 is advanced into the aperture 84 defined in the handle body 58. The arms 94, 100 of the rod 86 are advanced into contact with the inner walls 82, 80, respectively, of the handle body 58 that define the aperture 84. When the spring arm 100 engages the inner wall 80, the spring arm 100 moves relative to the support arm 94 from the uncompressed position to the compressed position, thereby permitting the rod 86 to advance along the inner walls 82, 80 of the handle body 58 such that the position indicator 42 is assembled with the tool 40.

The acetabular prosthetic component 10 may also be attached to the tool 40. To do so, the passageway 32 defined in the acetabular shell component 14 is aligned with the shaft 44 of the tool 40. The acetabular shell component 14 may be advanced into contact with the end 48 of the shaft 44 such that the threads 34 of the acetabular shell component 14 engage the threads 46 of the shaft 44. One of the tool 40 and the acetabular shell component 14 may then be rotated relative to the other component to thread the acetabular shell component 14 onto the end 48 of the shaft 44, thereby securing the acetabular shell component 14 to the surgical tool 40.

With the acetabular shell component 14 secured to the surgical tool 40, the acetabular shell component 14 may be advanced into the patient's surgically-prepared acetabulum 16, as shown in FIG. 5. To do so, the patient may be placed into a right or left lateral decubitus position such that the patient's surgically-prepared acetabulum 16 faces upward. As shown in FIG. 6, in the lateral decubitus position, the patient's body 140 defines a transverse axis 142 that extends parallel to the ground, as indicated by an imaginary axis 144. The patient's body 140 also defines a coronal plane 146, and a coronal axis 148 extends orthogonally to the coronal plane 146 and the transverse axis 142.

A user may utilize the tool 40 to rotate the acetabular shell component 14 to an initial predetermined position within the patient's surgically-prepared acetabulum 16. As shown in FIG. 6, the surgical tool 40 is located in the coronal plane 146 defined by the patient's body 140 such that the longitudinal axis 54 of the surgical tool 40 and the longitudinal axis 88 of the position indicator 42 are located in the coronal plane 146. While maintaining the surgical tool 40 in the coronal plane 146, a user may rotate the surgical tool 40 about the coronal axis 148 to move the acetabular shell component 14. As the surgical tool 40 is pivoted about the axis 148, the bubble 120 is moved within the vial 116 of the position indicator 42.

Figure 7:
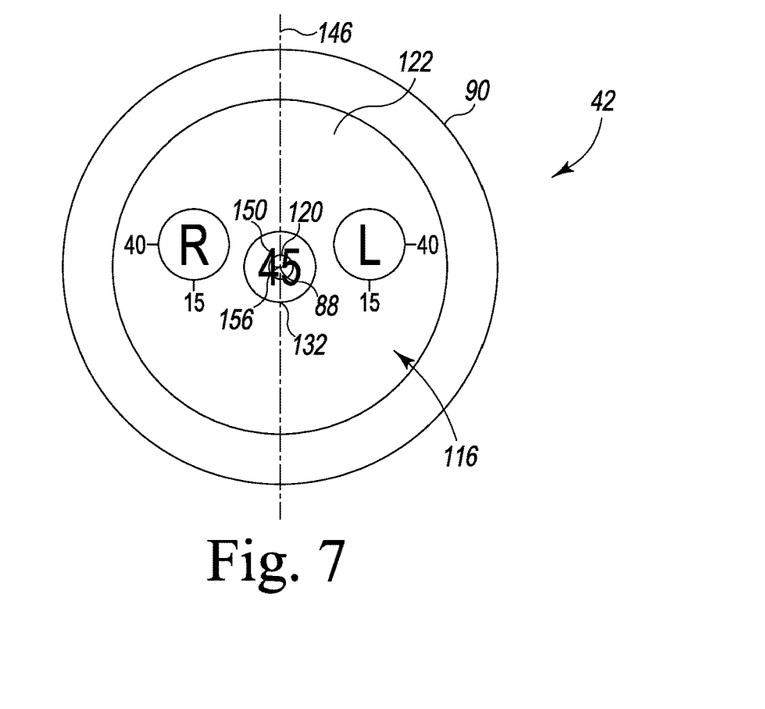
FIG. 7 is a front elevation view of the position indicator of the orthopaedic surgical instrument assembly when the orthopaedic surgical instrument assembly is positioned in the predetermined position of FIG. 6.

As shown in FIG. 7, the acetabular shell component 14 is located in the initial predetermined position when the bubble 120 is aligned with the ring 132 defined on the face plate 122 of the vial 116. The longitudinal axis 88 of the position indicator 42 extends outwardly through the center 156 of the face plate 122, and the ring 132 is aligned with the center 156. In the initial predetermined position, the coronal plane 146 is aligned with the longitudinal axis 88 and bisects the ring 132, as shown in FIG. 7.

As shown in FIG. 6, an angle α is defined between the longitudinal axis 54 of the surgical tool 40 and the transverse axis 142 at the predetermined position corresponding to the ring 132. In the illustrative embodiment, the angle α is equal to a predetermined amount of rotation about the coronal axis 148 and a predetermined abduction angle. The face plate 122 of the position indicator 42 includes a numerical indicator 150 that indicates to the user the magnitude of the angle α, as shown in FIG. 7. In the illustrative embodiment, the angle α has a magnitude of 45 degrees.

As shown in FIG. 8, the user may utilize the tool 40 to rotate the acetabular shell component 14 from the initial predetermined position to another predetermined position within the patient's surgically-prepared acetabulum 16. To do so, a user may rotate the surgical tool 40 about the transverse axis 142 and/or the coronal axis 148 to move the acetabular shell component 14. In the illustrative embodiment, the user rotates the surgical tool 40 about the transverse axis 142 such that the surgical tool 40 is angled out of the coronal plane 146. As shown in FIG. 8, the surgical tool 40 is rotated anteriorly relative to the coronal plane 146. The user also rotates the surgical tool 40 relative to the coronal axis 148.

Figure 9:
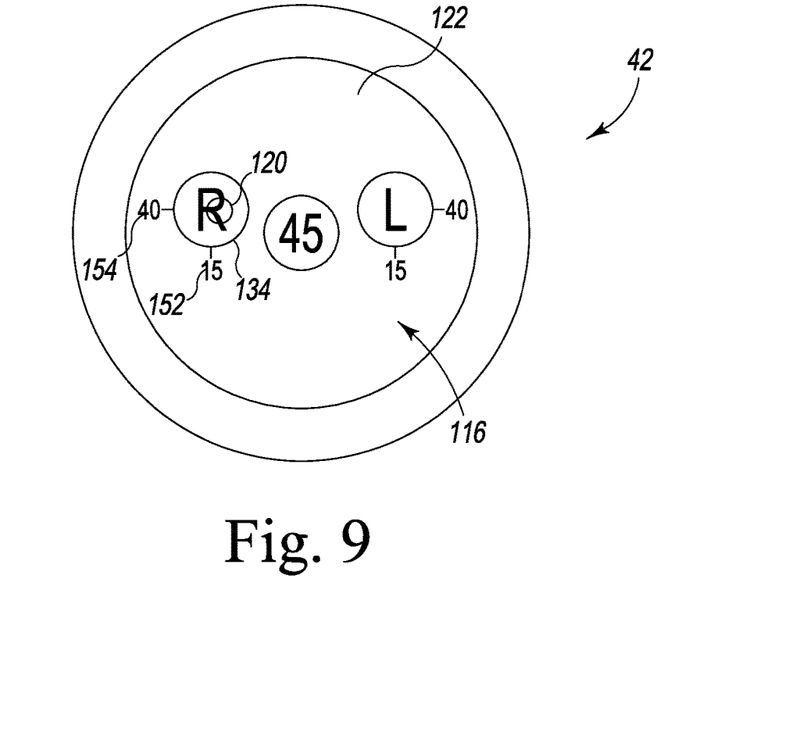
FIG. 9 is a front elevation view of the position indicator of the orthopaedic surgical instrument assembly when the orthopaedic surgical instrument assembly is positioned in the predetermined position of FIG. 8.

As the surgical tool 40 is pivoted about the axes 142, 148, the bubble 120 is moved within the vial 116 of the position indicator 42. As shown in FIG. 9, the acetabular shell component 14 is located in the second predetermined position when the bubble 120 is aligned with the ring 134 defined on the face plate 122 of the vial 116.

As shown in FIG. 8, an angle β is defined between the longitudinal axis 54 of the surgical tool 40 and the coronal plane 146 at the predetermined position corresponding to the ring 134. In the illustrative embodiment, the angle β is equal to a predetermined amount of rotation about the transverse axis 142 and a predetermined anteversion angle. As shown in FIG. 10, an angle φ is defined between the longitudinal axis 54 of the surgical tool 40 and the transverse axis 142 at the predetermined position corresponding to the ring 134. In the illustrative embodiment, the angle φ is equal to a predetermined amount of rotation about the coronal axis and a predetermined abduction angle. The face plate 122 of the position indicator 42 includes numerical indicators 152, 154 that indicate to the user the magnitudes of the angles β, φ, as shown in FIG. 9. In the illustrative embodiment, the angle β has a magnitude of 15 degrees the angle φ has a magnitude of 40 degrees.

It should be appreciated that the magnitudes of the angles α, β, φ may vary according to anatomy of a particular patient. For example, the magnitude of the angles α, φ may be between 35 degrees and 50 degrees, or, for example, the magnitude of the angle β may be between 15 and 30 degrees.

It should be appreciated that different position indicators with markings indicating different predetermined positions may be used during the installation process. In other embodiments, the position indicator may be a customized, patient-specific position indicator. As used herein, the term "customized, patient-specific" refers to a structure that has been created for use with a single patient. For example, the position indicator may include markings corresponding to custom, predetermined positions of the acetabular prosthetic component that are unique to a particular patient. In other embodiments, the markings of the position indicator may be based on surgeon-preferences.

Additionally, while the assembly 12 is used with the acetabular prosthetic component 10 in the procedure outlined above, the assembly 12 may also be used with an acetabular prosthetic trial component. When attached to a trial component, the user may use the assembly 12 to determine the type, configuration, and installed position of the acetabular prosthetic component that is to be implanted. It should be appreciated that different position indicators with markings indicating different predetermined positions may be used during the trialing process to determine the installed position of the acetabular prosthetic component.

Figure 11:
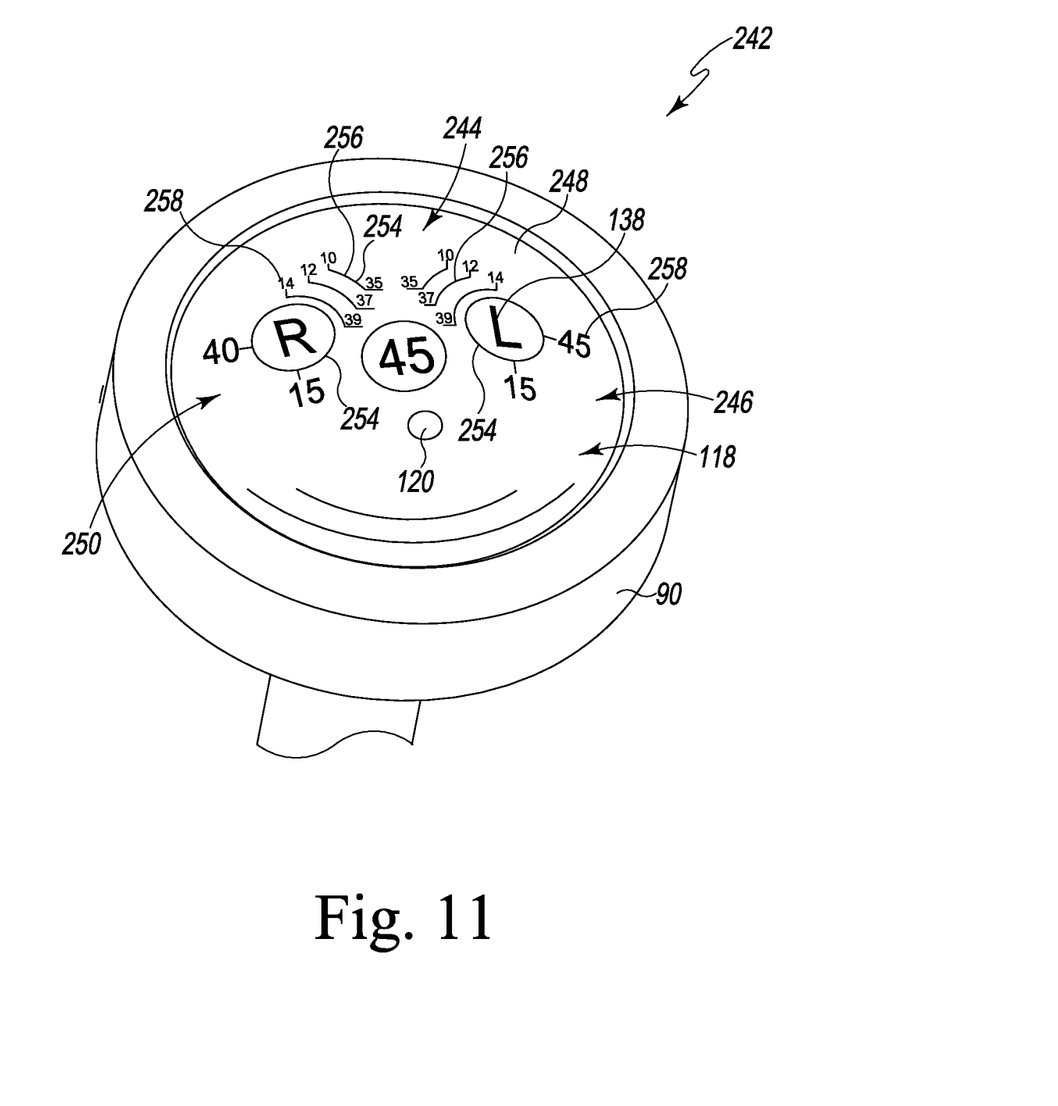
FIG. 11 is a perspective view of another embodiment of a position indicator of the orthopaedic surgical instrument assembly of FIG. 1.

Referring now to FIG. 11, another embodiment of a position indicator (hereinafter position indicator 242) is shown. Some features of the embodiment illustrated in FIG. 11 are substantially similar to those discussed above in reference to the embodiment of FIGS. 1-10. Such features are designated in FIG. 11 with the same reference numbers as those used in FIGS. 1-10. The position indicator 242, like the position indicator 42, is configured to be attached to the surgical tool 40.

The position indicator 242 includes a housing 90 and a rod (not shown) sized to be received in the aperture 84 of the handle body 58. The position indicator 242 includes a bubble indicator 244 having a vial 246 that defines a dome-shaped chamber 118 filled with a fluid such as, for example, isopropyl alcohol. Like the vial 116 of the position indicator 42, a bubble 120 is trapped within the chamber 118. Gravity and the physical difference between the gas of the bubble 120 and the fluid in the chamber 118 control the function of the bubble indicator 244, with the bubble 120 floating toward the side of the vial 246 that constitutes the high side of the vial 246.

The vial 246 of the bubble indicator 244 has a face plate 248 that is substantially transparent. In that way, a user may look through the face plate 248 to determine the position of the bubble 120. As shown in FIG. 11, the bubble indicator 244 has a plurality of markings 250 etched into an outer surface 252 of the face plate 248. Each of the markings 250 corresponds to a predetermined position of the acetabular prosthetic component 10 within the patient's surgically-prepared acetabulum 16.

In the illustrative embodiment, the markings 250 of the bubble indicator 244 include a plurality of graphical indicators 254 that correspond to a plurality of predetermined positions of the acetabular prosthetic component 10. As shown in FIG. 11, the graphical indicators 254 include rings 132, 134, 136, which correspond to the angles α, β, φ described above in reference to the embodiment of FIGS. 1-10. The graphical indicators 254 of the bubble indicator 244 also include a plurality of additional arcs 256 that correspond to additional predetermined positions of the acetabular prosthetic component 10. In the illustrative embodiment, the markings 254 also include a plurality of numerical indicators 258 that are associated with the graphical indicators 254 and indicate to the user the magnitude of the angles α, β, φ at various predetermined positions.

In use, the position indicator 242 may be used by a surgeon to determine the proper position of the acetabular prosthetic component 10 from the plurality of predetermined positions indicated by the markings 250. For example, when used with an acetabular prosthetic trial component, the user may use the position indicator 242 to determine the type, configuration, and installed position of the acetabular prosthetic component 10 by moving the acetabular prosthetic component 10 between multiple predetermined positions.

Figure 12:
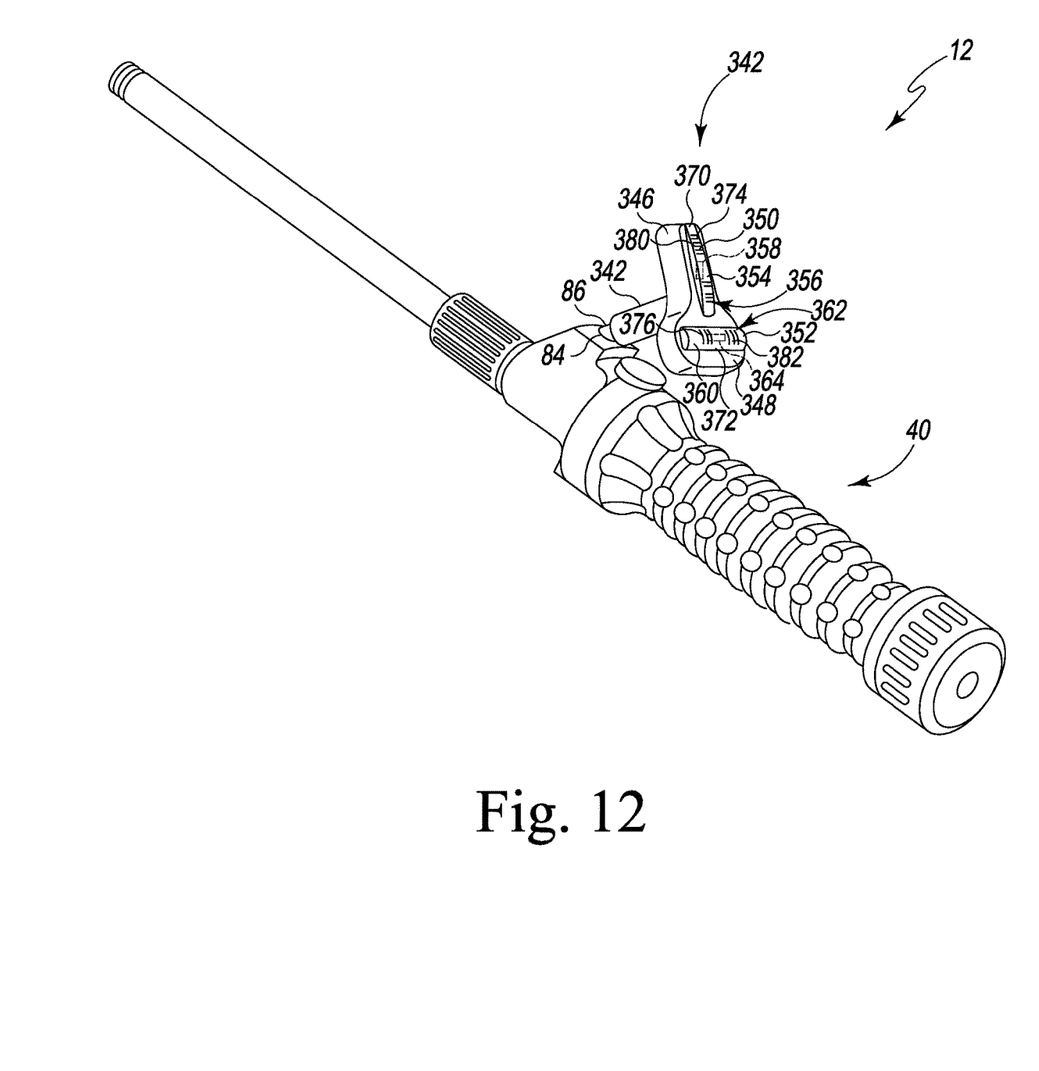
FIG. 12 is a perspective view of another embodiment of a position indicator of the orthopaedic surgical instrument assembly of FIG. 1.

Referring now to FIG. 12, another embodiment of a position indicator (hereinafter indicator 342) is shown attached to the surgical tool 40. Some features of the embodiment illustrated in FIG. 12 are substantially similar to those discussed above in reference to the embodiment of FIGS. 1-10. Such features are designated in FIG. 12 with the same reference numbers as those used in FIGS. 1-10. The position indicator 242, like the position indicator 42, is configured to be attached to the surgical tool 40.

The position indicator 342 includes a housing 344 and a rod 86 sized to be received in the aperture 84 of the handle body 58. The housing 344 includes an arm 346 that extends parallel to the longitudinal axis 54 of surgical tool 40 and a base 348 that extends orthogonal to the arm 346. As shown in FIG. 12, the position indicator 342 includes a bubble indicator 350 secured to the arm 346 and another bubble indicator 352 secured to the base 348.

The bubble indicator 350 includes an oblong-shaped vial 354 that extends parallel to the axis 54 of the surgical tool 40. The vial 354 defines a chamber 356 filled with a fluid such as, for example, isopropyl alcohol, and a bubble 358 is trapped within the chamber 356. The bubble indicator 352 includes an oblong-shaped vial 360 that extends orthogonal to the vial 354. The vial 360 defines a chamber 362 filled with a fluid, and a bubble 364 is trapped within the chamber 362. Gravity and the physical difference between the gas of the bubbles 358, 364 and the fluid in the chamber 356, 362, respectively, control the function of the bubble indicators 350, 352, with the bubbles 358, 364 floating toward the high sides of the vials 354, 360.

Each of the bubble indicators 350, 352 includes a face plate 370, 372, respectively. The face plates 370, 372 are substantially transparent. In that way, a user may look through the face plates 370, 372 to determine the respective positions of the bubbles 350, 352. The face plate 370 has a plurality of markings 374 that indicate a plurality of predetermined positions of the acetabular prosthetic component 10 within the patient's surgically-prepared acetabulum 16. In the illustrative embodiment, the markings 374 correspond to predetermined amounts of rotation about the coronal axis 148 and predetermined abduction angles.

The face plate 372 of the bubble indicator 352 has a plurality of markings 376 that indicate a plurality of predetermined positions of the acetabular prosthetic component 10 within the patient's surgically-prepared acetabulum 16. In the illustrative embodiment, the markings 376 correspond to predetermined amounts of rotation about the transverse axis 142 and predetermined anteversion angles.

In the illustrative embodiment, the markings 374, 376 of the bubble indicator 350, 352 include a plurality of graphical indicators 380, 382 that correspond to a plurality of predetermined positions of the acetabular prosthetic component 10 within the patient's surgically-prepared acetabulum 16. It should be appreciated that in other embodiments the markings 374, 376 may include numerical or side indicators similar to those described above in regard to FIGS. 1-10.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of positioning an acetabular prosthetic component in a patient's surgically-prepared acetabulum, the method comprising:
    rotating an acetabular prosthetic component in a patient's surgically-prepared acetabulum until a bubble of a bubble indicator is substantially aligned with a first marking, the first marking indicating a first position of the acetabular prosthetic component, and
    rotating the acetabular prosthetic component anteriorly until the bubble is substantially aligned with a second marking, the second marking indicating a second position of the acetabular prosthetic component,
    wherein the acetabular prosthetic component is at a first abduction angle in the first position, and the acetabular prosthetic component is at a second abduction angle in the second position, the second abduction angle being less than the first abduction angle.

2. The method of claim 1, wherein the first abduction angle is approximately 45 degrees.

3. The method of claim 1, wherein the second abduction angle is approximately 40 degrees.

4. The method of claim 3, wherein rotating the acetabular prosthetic component anteriorly includes rotating the acetabular prosthetic component approximately 15 degrees about a transverse axis extending through the patient.

5. The method of claim 1, wherein rotating the acetabular prosthetic component in the patient's surgically-prepared acetabulum includes maintaining alignment between the first marking and the coronal plane.

6. A method of positioning an acetabular prosthetic component in a patient's surgically-prepared acetabulum, the method comprising:
    selecting a bubble indicator from a plurality of bubble indicators,
    attaching the bubble indicator to a surgical tool,
    threading an acetabular prosthetic component onto the surgical tool,
    rotating the acetabular prosthetic component in a patient's surgically-prepared acetabulum until a bubble of the bubble indicator is substantially aligned with a first marking, the first marking indicating a first position of the acetabular prosthetic component, and
    rotating the acetabular prosthetic component anteriorly until the bubble is substantially aligned with a second marking, the second marking indicating a second position of the acetabular prosthetic component.

7. The method of claim 1, wherein rotating the acetabular prosthetic component in the patient's surgically-prepared acetabulum until the bubble of the bubble indicator is substantially aligned with the first marking includes aligning a graphical indicator of the first marking with the bubble of the bubble indicator.

8. The method of claim 6, wherein the acetabular prosthetic component is at a first abduction angle in the first position, and the acetabular prosthetic component is at a second abduction angle in the second position, the second abduction angle being less than the first abduction angle.

9. The method of claim 8, wherein the first abduction angle is approximately 45 degrees.

10. The method of claim 6, wherein rotating the acetabular prosthetic component anteriorly includes rotating the acetabular prosthetic component approximately 15 degrees about a transverse axis extending through the patient.

11. The method of claim 6, wherein rotating the acetabular prosthetic component in the patient's surgically-prepared acetabulum until the bubble of the bubble indicator is substantially aligned with the first marking includes aligning a graphical indicator of the first marking with the bubble of the bubble indicator.

12. A method of positioning an acetabular prosthetic component in a surgically-prepared acetabulum of a patient's body, the method comprising:
    positioning a bubble indicator in a coronal plane defined by a patient's body such that a first marking is aligned with the coronal plane,
    rotating an acetabular prosthetic component in a surgically-prepared acetabulum of the patient's body until a bubble of the bubble indicator is substantially aligned with the first marking, the first marking indicating a first position of the acetabular prosthetic component, and
    rotating the acetabular prosthetic component anteriorly until the bubble is substantially aligned with a second marking, the second marking indicating a second position of the acetabular prosthetic component,
    wherein rotating the acetabular prosthetic component in the surgically-prepared acetabulum of the patient's body includes maintaining alignment between the first marking and the coronal plane.

13. The method of claim 12, wherein the acetabular prosthetic component is at a first abduction angle in the first position, and the acetabular prosthetic component is at a second abduction angle in the second position, the second abduction angle being less than the first abduction angle.

14. The method of claim 13, wherein rotating the acetabular prosthetic component anteriorly includes rotating the acetabular prosthetic component approximately 15 degrees about a transverse axis extending through the patient.

15. The method of claim 12, wherein rotating the acetabular prosthetic component in the surgically-prepared acetabulum until the bubble of the bubble indicator is substantially aligned with the first marking includes aligning a graphical indicator of the first marking with the bubble of the bubble indicator.

16. The method of claim 12, further comprising:
    selecting the bubble indicator from a plurality of bubble indicators,
    attaching the bubble indicator to a surgical tool, and
    threading the acetabular prosthetic component onto the surgical tool.

* * * * *